United States Patent
Porter et al.

(10) Patent No.: US 9,446,043 B2
(45) Date of Patent: Sep. 20, 2016

(54) PHARMACEUTICAL COMBINATIONS

(71) Applicant: Novartis AG, Basel (CH)

(72) Inventors: Dale Porter, Cambridge, MA (US); Caroline Emery, Cambridge, MA (US); Lujian Tan, Cambridge, MA (US); Padmaja Yerramilli-Rao, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/647,939

(22) PCT Filed: Nov. 26, 2013

(86) PCT No.: PCT/US2013/071852
§ 371 (c)(1),
(2) Date: May 28, 2015

(87) PCT Pub. No.: WO2014/085381
PCT Pub. Date: Jun. 5, 2014

(65) Prior Publication Data
US 2015/0306101 A1  Oct. 29, 2015

Related U.S. Application Data

(60) Provisional application No. 61/731,174, filed on Nov. 29, 2012, provisional application No. 61/731,555, filed on Nov. 30, 2012, provisional application No. 61/755,520, filed on Jan. 23, 2013.

(51) Int. Cl.
*A61K 31/517* (2006.01)
*A61K 31/496* (2006.01)
(Continued)

(52) U.S. Cl.
CPC ........... *A61K 31/517* (2013.01); *A61K 31/404* (2013.01); *A61K 31/4025* (2013.01); *A61K 31/4184* (2013.01); *A61K 31/496* (2013.01); *A61K 31/506* (2013.01); *A61K 45/06* (2013.01)

(58) Field of Classification Search
CPC ............ A61K 31/517; A61K 31/496; A61K 31/4184; A61K 31/404; A61K 31/4025
USPC .......... 514/250, 252, 252.12, 299, 207, 397, 514/408, 412
See application file for complete search history.

(56) References Cited

U.S. PATENT DOCUMENTS 5,489,608 A  2/1996 Kleinschroth et al.
5,545,636 A  8/1996 Heath et al.
(Continued)

FOREIGN PATENT DOCUMENTS

EP  0776895  10/1998
EP  0817627  3/2005
(Continued)

OTHER PUBLICATIONS

Xinqi et al, "The Protein Kinase C Inhibitor Enzastaurin Exhibits Antitimor Activity against Uveal Melanoma," PLoS One, vol. 7(1), received Jun. 29, 2011.*
(Continued)

*Primary Examiner* — Kamal A. Saeed
*Assistant Examiner* — Janet L Coppins
(74) *Attorney, Agent, or Firm* — Fish & Richardson P.C.

(57) ABSTRACT

A pharmaceutical combination comprising (a) a protein kinase C (PKC) inhibitor compound, or a pharmaceutically acceptable salt thereof, and (b) at least one mitogen activated protein kinase (MEK) inhibitor or a pharmaceutically acceptable salt, and optionally a pharmaceutically acceptable carrier, for simultaneous, separate or sequential administration; the uses of such combination in the treatment of proliferative diseases; and methods of treating a subject suffering from a proliferative disease comprising administering a therapeutically effective amount of such combination.

19 Claims, 8 Drawing Sheets

(51) Int. Cl.
  *A61K 31/4184* (2006.01)
  *A61K 31/4025* (2006.01)
  *A61K 31/404* (2006.01)
  *A61K 45/06* (2006.01)
  *A61K 31/506* (2006.01)

(56) References Cited

U.S. PATENT DOCUMENTS

| | | | |
|---|---|---|---|
| 5,668,152 | A | 9/1997 | Heath, Jr. et al. |
| 5,672,681 | A | 9/1997 | Kahn |
| 5,698,578 | A | 12/1997 | Heath, Jr. et al. |
| 5,710,145 | A | 1/1998 | Engel et al. |
| 6,645,970 | B2 | 11/2003 | Albert et al. |
| 7,220,774 | B2 | 5/2007 | Albert et al. |
| 7,235,555 | B2 | 6/2007 | Evenou et al. |
| 8,193,229 | B2 | 6/2012 | Wallace et al. |
| 8,193,230 | B2 | 6/2012 | Wallace et al. |
| 8,513,293 | B2 | 8/2013 | Wallace et al. |
| 2008/0318975 | A1 | 12/2008 | Schuler et al. |

FOREIGN PATENT DOCUMENTS

| | | |
|---|---|---|
| EP | 1337527 | 10/2009 |
| EP | 1449529 | 1/2010 |
| WO | WO 02/06213 | 1/2002 |
| WO | WO 02/38561 | 5/2002 |
| WO | WO 03/077914 | 9/2003 |
| WO | WO 03/082859 | 10/2003 |
| WO | WO 2005/121142 | 12/2005 |
| WO | WO 2007/006533 | 1/2007 |
| WO | WO 2007/044084 | 4/2007 |

OTHER PUBLICATIONS

Xinqi et al, "The Protein Kinase C Inhibitor Enzastaurin Exhibits Antitimor Activity against Uveal Melanoma," PLoS One, vol. 7(1), 2012.*

Chou and Talalay, "Quantitative analysis of dose-effect relationships: the combined effects of multiple drugs or enzyme inhibitors," Adv. Enzyme Regul., 1984, 22:27-55.

Goto et al., "E6201 [(3S,4R,5Z,8S,9S,11E)-14-(ethylamino)-8, 9,16-trihydroxy-3,4-dimethyl-3,4,9,19-tetrahydro-1H-2-benzoxacyclotetradecine-1,7(8H)-dione], a novel kinase inhibitor of mitogen-activated protein kinase/extracellular signal-regulated kinase kinase (MEK)-1 and MEK kinase-1: in vitro characterization of its anti-inflammatory and antihyperproliferative activities," J. Pharmacology and Experimental Therapeutics, 2009, 3331(2):485-495.

Holford and Scheiner, "Understanding the dose-effect relationship: clinical application of pharmacokinetic-pharmacodynamic models," Clin. Pharmacokinet, 1981, 6:429-453.

International Preliminary Report on Patentability in International Application No. PCT/US2013/071852, dated Jun. 2, 2015, 22 pages.

International Search Report in International Application No. PCT/US2013/071852, dated Jan. 20, 2014, 14 pages.

Lee et al., "Abstract 2515: Preclinical Development of ARRY-162, a Potent and Selective MEK 1/2 Inhibitor," Cancer Research, Apr. 2010, 70(8):2515.

Loewe and Muischnek, Arch. Exp. Pathol Pharmacol., 1926, 114:313-326.

Velho et al., "New therapeutic agents in uveal melanoma," Anticancer research, Jul. 2012, 2591.

Woessner et al., "Abstract 2514: ARRY-162, A Potent and Selective MEK 1/2 Inhibitor, Shows Enhance Efficacy in Combination with Other Targeted Kinase Inhibitors and with Chemotherapy," Cancer Research, Apr. 2010, 70(8):2514.

Written Opinion in International Application No. PCT/US2013/071852, dated Jan. 20, 2014, 21 pages.

Wu et al., "Protein Kinase C Inhibitor AEB071 Targets Ocular Melanoma Harboring GNAQ Mutations via Effects on the PKC/Erk1/2 and PKC/NF—B Pathways," Molecular Cancer Therapeutics, Sep. 2012, 11(9):1905-1914.

Wu et al., "The Protein Kinase C Inhibitor Enzastaurin Exhibits Antitumor Activity against Uveal Melanoma," PLOS One, Jan. 2012, 7(1):1-10.

* cited by examiner

PHARMACEUTICAL COMBINATIONS

CROSS REFERENCE TO RELATED APPLICATIONS

This application is a National Stage application under 35 U.S.C. 371 of International Application No. PCT/US2013/071852, having an International Filing Date of Nov. 26, 2013, which claims the benefit of U.S. Provisional Ser. No. 61/731,174, filed Nov. 29, 2012, U.S. Provisional Ser. No. 61/731,555, filed Nov. 30, 2012, and U.S. Provisional Ser. No. 61/755,520, filed Jan. 23, 2013. The disclosures of the prior applications are considered part of (and are incorporated by reference in) the disclosure of this application.

FIELD OF THE INVENTION

The present invention relates to a pharmaceutical combination comprising (a) a protein kinase C (PKC) inhibitor compound, or a pharmaceutically acceptable salt thereof, and (b) one, or at least one, mitogen activated protein kinase (MEK) inhibitor compound, or a pharmaceutically acceptable salt thereof, and optionally at least one pharmaceutically acceptable carrier; the uses of such a combination in the treatment or prevention of proliferative diseases, such as cancer; and methods of treating a subject suffering from a proliferative disease, such as cancer, comprising administering a therapeutically effective amount of such a combination.

The present invention also relates to a pharmaceutical combination comprising (a) a protein kinase C (PKC) inhibitor compound 3-(1H-indol-3-yl)-4-[2-(4-methyl-piperazin-1-yl)-quinazolin-4-yl]-1H-pyrrole-2,5-dione or a pharmaceutically acceptable salt thereof, and (b) at least one mitogen activated protein kinase (MEK) inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally at least one pharmaceutically acceptable carrier; the uses of such a combination in the treatment or prevention of proliferative diseases, such as cancer; and methods of treating a subject suffering from a proliferative disease, such as cancer, comprising administering a therapeutically effective amount of such a combination.

BACKGROUND OF THE INVENTION

Uveal melanoma is a malignant neoplasm that arises in the pigmented portions of the eye, specifically in the iris, ciliary body or choroid. Therapy for uveal melanoma includes local therapy with enucleation or brachytherapy. Approximately half of patients develop metastatic disease, typically to the liver and often to lung and bone, and the incidence of new metastases continues to increase with time suggesting that the disease is slow growing. The outcome for patients with metastatic disease is dismal. No therapy for this disease has been approved to date.

Mutations affecting either one of two genes that encode G protein alpha subunits of heterotrimeric G protein complexes (GNAQ and GNA11) were discovered in the vast majority of tumors (Van Raamsdonk C D, Bezrookove V, Green G, et al, Nature (2009); 457:599-601 and Van Raamsdonk C D, Griewank K G, et al (2010), N Eng J Med; 363:2191-9). The mutations identified are typical of activating mutations affecting other G proteins.

In spite of numerous treatment options for patients with cancer, there remains a need for effective and safe therapeutic agents and a need for new combination therapies that can be administered for the effective long-term treatment of cancer.

The present inventors have now found that inhibition of the signaling cascade downstream of these G proteins may be useful for the treatment of a proliferative disease such as cancer, e.g. a tumor with a Ga mutation (GNA11/GNAQ), and in particular, uveal melanoma, metastatic uveal melanoma, and GNAQ or GNA11 mutant uveal melanoma.

It has now been found that a combination of a protein kinase C (PKC) inhibitor compound and a MEK inhibitor compound is effective for the delay of progression or treatment of a proliferative disease, especially uveal melanoma, metastatic uveal melanoma, and GNAQ or GNA11 mutant uveal melanoma.

It has now been surprisingly discovered that the combination of an effective amount of a protein kinase C (PKC) inhibitor, e.g. 3-(1H-indol-3-yl)-4-[2-(4-methyl-piperazin-1-yl)-quinazolin-4-yl]-1H-pyrrole-2,5-dione, or a pharmaceutically acceptable salt thereof, e.g. the acetate thereof, with an effective amount of at least one MEK inhibitor compound, e.g. 6-(4-bromo-2-fluorophenylamino)-7-fluoro-3-methyl-3H-benzoimidazole-5-carboxylic acid (2-hydroxyethoxy)-amide or (S)-5-fluoro-2-(2-fluoro-4-(methylthio)phenylamino)-N-(2-hydroxypropoxy)-1-methyl-6-oxo-1,6-dihydropyridine-3-carboxamide, more preferably, 6-(4-bromo-2-fluorophenylamino)-7-fluoro-3-methyl-3H-benzoimidazole-5-carboxylic acid (2-hydroxyethoxy)-amide, results in unexpected improvement in the treatment of proliferative diseases, particularly cancer, and more particularly uveal melanoma, metastatic uveal melanoma, and GNAQ or GNA11 mutant uveal melanoma.

When administered simultaneously, sequentially or separately, the preferred protein kinase C (PKC) inhibitor compound and the preferred MEK inhibitor compound interact in a synergistic manner to strongly inhibit cell proliferation and are surprisingly efficacious in uveal melanoma models This unexpected synergistic reaction allows reduction in the dose required for each compound, leading to a reduction in the side effects and enhancement of the long-term clinical effectiveness of the compounds in treatment.

SUMMARY OF THE INVENTION

The invention provides pharmaceutical combinations and therapeutic methods which may be useful for inhibiting the cell growth of a tumor with a Ga mutation (GNA11/GNAQ) and for treating proliferative diseases, particularly cancer, and more particularly uveal melanoma, metastatic uveal melanoma, and GNAQ or GNA11 mutant uveal melanoma.

The present invention provides pharmaceutical combinations comprising: (a) a protein kinase C (PKC) inhibitor, or a pharmaceutically acceptable salt thereof, and (b) at least one mitogen activated protein kinase (MEK) inhibitor and optionally at least one pharmaceutically acceptable carrier.

The present invention also provides pharmaceutical combinations consisting of: (a) a protein kinase C (PKC) inhibitor, or a pharmaceutically acceptable salt thereof, and (b) one mitogen activated protein kinase (MEK) inhibitor and optionally at least one pharmaceutically acceptable carrier.

In the above combinations, the PKC inhibitor compound may be selected from the group consisting of 3-(1H-indol-3-yl)-4-[2-(4-methyl-piperazin-1-yl)-quinazo-lin-4-yl]-1H-pyrrole-2,5-dione;

3-(1.H.-indol-3-yl)-4-[2-(piperazin-1-yl)-quinazolin-4-yl]-1H-pyrrole-2,5-dione;

3-[2-chloro-7-[(dimethylamino)methyl]-1-naphthalenyl]-4-[7-[2-(2-methoxyethoxyl)ethoxy]-1H-indol-3-yl]-1H-pyrrole-2,5-dione;

3-[3-(4,7-diaza-spiro[2,5]oct-7-yl)-isoquinolin-1-yl]-4-(7-methyl-1H-indol-3-yl)-pyrrole-2,5-dione, (9S)-9-[(dimethylamino)methyl]-6,7,10,11-tetrahydro-9H,18H-5,21:12,17-dimethenodibenzo-[e,k]pyrrolo[3,4-h][1,4,13]oxadiazacyclohexadecine-18,20(19H)-dione, ruboxistaurin, and and 12-(2-cyanoethyl)-6,7,12,13-tetrahydro-13-methyl-5-oxo-5H-indolo(2,3-a)pyrrolo(3,4-c)-carbazole, or a pharmaceutically acceptable salt thereof.

In the above combinations, the MEK inhibitor compound may be independently selected from the PKC inhibitor and may be selected from the group consisting of 6-(4-bromo-2-fluorophenylamino)-7-fluoro-3-methyl-3H-benzoimidazole-5-carboxylic acid (2-hydroxy-ethoxy)-amide, (S)-5-fluoro-2-(2-fluoro-4-(methyl-thio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, R04987655, JTP-74057, RG7167, and RG7420, or a pharmaceutically acceptable salt thereof, The present invention also provides a pharmaceutical combination comprising: (a) a protein kinase C (PKC) inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) at least one mitogen activated protein kinase (MEK) inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, and optionally at least one pharmaceutically acceptable carrier.

In a preferred embodiment of the present invention, the combination partners are (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) at least one MEK inhibitor compound selected from the group consisting of 6-(4-bromo-2-fluorophenylamino)-7-fluoro-3-methyl-3H-benzoimidazole-5-carboxylic acid (2-hydroxy-ethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) or a pharmaceutically acceptable salt thereof.

In another preferred embodiment of the present invention, the combination partners are (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) or a pharmaceutically acceptable salt thereof.

The present invention further relates to a combined preparation or a pharmaceutical composition comprising (a) a PKC inhibitor compound 3-(1.H.-indol-3-yl)-4-[2-(4-methyl-piperazin-1-yl)-quinazolin-4-yl]-pyrrole-2,5-dione (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, and optionally at least one pharmaceutically acceptable carrier. In one embodiment, the present invention relates to a combined preparation which comprises: (i) one or more unit dosage forms of combination partner (a), and (ii) one or more unit dosage forms of combination partner (b).

The present invention particularly pertains to a pharmaceutical combination comprising (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, and optionally at least one pharmaceutically acceptable carrier useful for treating or preventing a proliferative disease in a subject in need thereof.

The present invention also pertains to a pharmaceutical combination comprising (a) a PKC inhibitor compound 3-(1H-indol-3-yl)-4-[2-(4-methyl-piperazin-1-yl)-quinazo-lin-4-yl]-1H-pyrrole-2,5-dione (COMPOUND A) or a pharmaceutically acceptable salt thereof, and (b) at least one MEK inhibitor selected from the group comprising 6-(4-bromo-2-fluorophenylamino)-7-fluoro-3-methyl-3H-benzo-imidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, and optionally at least one pharmaceutically acceptable carrier for use in the preparation of a pharmaceutical composition or medicament for the treatment or prevention of a proliferative disease in a subject in need thereof.

The present invention further pertains to the use of a PKC inhibitor 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, in combination with at least one MEK inhibitor selected from the group comprising 6-(4-bromo-2-fluorophenylamino)-7-fluoro-3- methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof for the preparation of a pharmaceutical composition or medicament for the treatment or prevention of a proliferative disease.

The present invention relates to a method of treating a subject having a proliferative disease comprising administered to said subject a combination comprising (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, and optionally at least one pharmaceutically acceptable carrier in a quantity, which is jointly therapeutically effective against a proliferative disease.

The present invention further provides a commercial package comprising as therapeutic agents a combination comprising (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, R04987655, JTP-74057, RG7167, or RG7420 or a pharmaceutically acceptable salt thereof, together with instructions for simultaneous, separate or sequential administration thereof for use in the delay of progression or treatment of a proliferative disease.

The above combinations are also provided for simultaneous, separate or sequential administration, in particular for treating or preventing a proliferative disease.

The proliferative disease is cancer, and more particularly uveal melanoma, metastatic uveal melanoma, GNAQ or GNA11 mutant uveal melanoma and cancer, and more particularly uveal melanoma, metastatic uveal melanoma, and GNAQ or GNA11 mutant metastatic uveal melanoma.

BRIEF DESCRIPTION OF THE FIGURES

As shown in FIG. 4 monotherapy AEB071 treatment resulted in a 3% T/C ($p<0.01$) and addition of COMPOUND B dosed twice daily at 3.5 mg/kg to the AEB071 regimen yielded a −22% T−T0 ($p<0.001$ median activity, but not significant compared to AEB071 alone). COMPOUND B had no activity in its own right in this in vivo model with a T/C of 84%. Treatment with AEB071 and COMPOUND B is thus efficacious in the 92.1 in vivo uveal melanoma model.

As shown in FIG. 6 monotherapy AEB071 at 90.95 mg/kg resulted in 18% T/C (p<0.05). AEB071 monotherapy with 45.5 and 22.7 mg/kg resulted in 52% and 92% T/C respectively, and non-significant median inhibition. Addition of COMPOUND B dosed twice daily at 3.5 mg/kg with AEB071 doses of 90.95 and 45.58 mg/kg yielded a −52% and −12% T−T0 respectively (p<0.001). COMPOUND B had no activity in its own right in this in vivo model with a T/C of 56%. The high dose combination yielded four partial regressions. Treatment at multiple doses of AEB071 in combination with COMPOUND B is efficacious in 92.1 in vivo uveal melanoma model. The effectiveness of the combination increases in a dose dependent manner, with increasing AEB071 dose in combination with COMPOUND B yielding a greater magnitude of response.

DETAILED DESCRIPTION OF THE INVENTION

Figure 1:
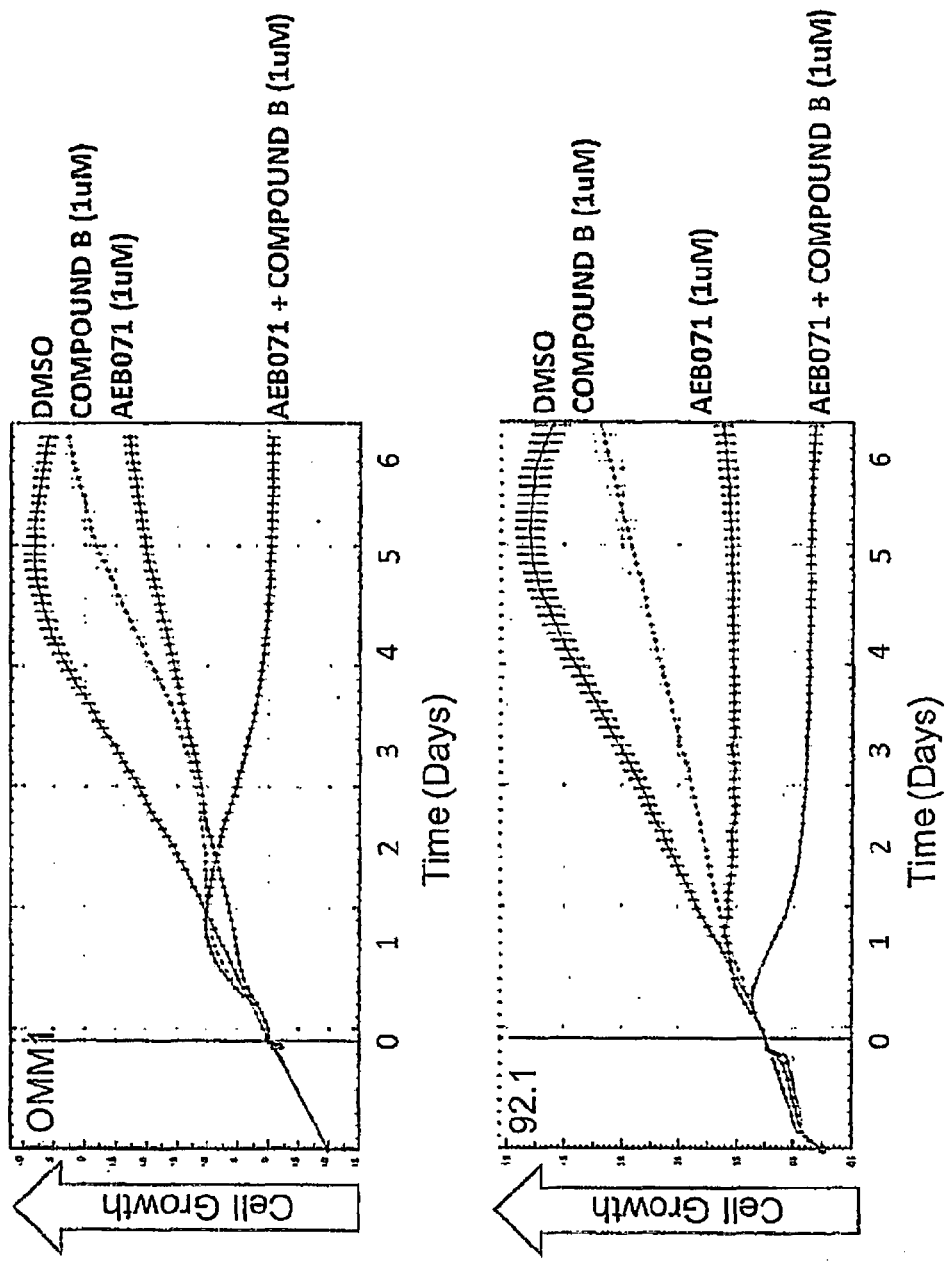
FIG. 1 shows the effect of 3-(1H-indol-3-yl)-4-[2-(4-methyl-piperazin-1-yl)-quinazolin-4-yl]-1H-pyrrole-2,5-dione (COMPOUND A) and 6-(4-bromo-2-fluorophenylamino)-7-fluoro-3-methyl-3H-benzoimidazole-5-carboxylic acid (2-hydroxyethoxy)-amide (COMPOUND B) on uveal melanoma proliferation in vitro. The growth of uveal melanoma cell lines over the course of 6 days was measured by xCELLigence technology in the presence of 0.5 µM DMSO, 0.5 µM AEB071, 0.5 µM COMPOUND B or 0.5 µM AEB071+0.5 µM COMPOUND B. In the 92.1 and OMM1 cell lines which possess GNAQ and GNA11 mutations respectively, AEB071 delayed cell growth, this effect was exacerbated when in combination with COMPOUND B. As COMPOUND B as a single agent had a modest effect on the growth of both uveal melanoma cell lines 92.1 and OMM1, the combination of the two agents was surprisingly able to fully suppress proliferation of both cell lines.

Various enumerated embodiments of the invention are described herein. It will be recognized that features specified in each embodiment may be combined with other specified features to provide further embodiments of the present invention.

The present invention provides pharmaceutical combinations comprising: (a) a protein kinase C (PKC) inhibitor, or a pharmaceutically acceptable salt thereof, and (b) at least one mitogen activated protein kinase (MEK) inhibitor and optionally at least one pharmaceutically acceptable carrier.

The present invention relates to such pharmaceutical combinations for simultaneous, separate or sequential administration, in particular for use in the treatment or prevention of a proliferative disease.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where the PKC inhibitor compound, e.g. COMPOUND A, or a pharmaceutically acceptable salt thereof, and at least one MEK inhibitor compound, e.g. COMPOUND B or COMPOUND C, or a pharmaceutically acceptable salt thereof, may be administered simultaneously, independently at the same time or separately within time intervals that allow that the combination partners to show a cooperative, e.g., synergistic, effect. The term "fixed combination" means that the active ingredients, e.g. a COMPOUND A and a combination partner, e.g. COMPOUND B, are both administered to a patient simultaneously in the form of a single entity or dosage. The term "non-fixed combination" means that the active ingredients, e.g. COMPOUND A, or a pharmaceutically acceptable salt thereof, and a combination partner, e.g. COMPOUND B, or a pharmaceutically acceptable salt thereof, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The term "a protein kinase C inhibitor" is defined herein to refer to a compound which targets, decreases or inhibits protein kinase C. The term PKC generally refers to the entire family of isoforms: conventional isoforms; alpha, beta ($\beta$1 and $\beta$2) and gamma, novel isoforms; delta, epsilon, eta, and theta, and atypical isoforms; zeta, and tau/lambda.

Suitable PKC inhibitors include maleimide derivatives, such as compounds described in U.S. Pat. Nos. 5,545,636; 5,668,152; 5,672,681; 5,698,578; 5,710,145; 6,645,970; 7,220,774; 7,235,555; US Publication No. 2008/0318975; European Patent Nos. 0776895 B1; 0817627 B1; 1449529 B1; 1337527 B1; and PCT Publication Nos. WO03/082859; and WO07/006533. Each of the references cited above are incorporated herein by reference.

Specific PKC inhibitor compounds of interest include sotrastaurin (also known as AEB071 and described in U.S. Pat. No. 6,645,970), 3-(1H-Indol-3-yl)-4-[2-(piperazin-1-yl)quinazolin-4-yl]-1H-pyrrole-2,5-dione described in Example 70 of PCT Publication No. WO 2002/038561 or U.S. Pat. No. 6,645,970), 3-[2-chloro-7-[(dimethylamino)methyl]-1-naphthalenyl]-4-[7-[2-(2-methoxyethoxyl)ethoxy]-1H-indol-3-yl]-1H-pyrrole-2,5-dione ((CAS No. 919992-85-1, described in PCT Publication No. WO07/006533 and US Publication No. 2008/0318975), 3-[3-(4,7-diaza-spiro[2,5]oct-7-yl)-isoquinolin-1-yl]-4-(7-methyl-1H-indol-3-yl)-pyrrole-2,5-dione (described in Example 69 of U.S. Pat. No. 7,235,555);

ruboxistaurin ((9S)-9-[(dimethylamino)methyl]-6,7,10,11-tetrahydro-9H, 18H-5,21:12,17-dimethenodibenzo-[e,k]pyrrolo[3,4-h][1,4,13]oxadiazacyclohexadecine-18,20 (19H)-dione (also known as LY-333531 and described in U.S. Pat. No. 5,698,578)) and the mesylate salt of ruboxistaurin (described in U.S. Pat. No. 5,710,145 and European patent No. 0776895 B1);

and 12-(2-cyanoethyl)-6,7,12,13-tetrahydro-13-methyl-5-oxo-5H-indolo(2,3-a)pyrrolo(3,4-c)-carbazole (CAS No. 136194-77-9, available from Calbiochem® and described in U.S. Pat. No. 5,489,608).

Other PKC inhibitors may be selected from the group consisting of AD 198, aprinocarsen, balanol, bryostatin 1, balphostin, cedefingol, CGP 53353, chelerythrine chloride, cycloplatam, delcasertib, enzastaurin, EP 70905, GF 109203X, gnidimacrin, GO 6976, GO 7716, GO 7775, GO 7852, HO 0303, ingenol mebutate, ISI 641, JTV 519, KAI 1678, LY 290181, LY 317644, midostaurin, NA 0345, NPC 15437, NSC 639365, NSC 639366, NSC 646958, p XSC, RD 65071, RO 317549, RO 318220, RO 318425, RO 318830, RO 320432, Safingol, SPC 104065, staurosporine, teprenone, tocopherol succinate, UCN 01 and UCN 1028C. In some embodiments, the PKC inhibitor is midostaurin, enzastaurin, or staurosporine. In some embodiments, the PKC inhibitor is 3-(1H-Indol-3-yl)-4-[2-(piperazin-1-yl) quinazolin-4-yl]-1H-pyrrole-2,5-dione described in Example 70 of PCT Publication No. WO 2002/038561 or U.S. Pat. No. 6,645,970), Each of the references cited above are incorporated herein by reference.

The term "a MEK inhibitor" is defined herein to refer to a compound which targets, decreases or inhibits the kinase activity of MAP kinase, MEK. A target of a MEK inhibitor includes, but is not limited to, ERK. An indirect target of a MEK inhibitor includes, but is not limited to, cyclin D1.

The term "pharmaceutical composition" is defined herein to refer to a mixture or solution containing at least one therapeutic agent to be administered to a subject, e.g., a mammal or human, in order to prevent or treat a particular disease or condition affecting the mammal or human.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human.

The term "prevent", "preventing" or "prevention" as used herein comprises the prevention of at least one symptom associated with or caused by the state, disease or disorder being prevented.

The term "jointly therapeutically active" or "joint therapeutic effect" as used herein means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "pharmaceutically effective amount" or "clinically effective amount" of a combination of therapeutic agents is an amount sufficient to provide an observable improvement over the baseline clinically observable signs and symptoms of the disorder treated with the combination.

The term "synergistic effect" as used herein refers to action of two therapeutic agents such as, for example, a compound of formula (I), e.g., Compound A, and a MEK inhibitor compound of the present invention, e.g., Compound B, producing an effect, for example, slowing the symptomatic progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancers.

The term about" or "approximately" shall have the meaning of within 10%, more preferably within 5%, of a given value or range.

Pharmaceutical combinations of the present invention may include PKC compound 3-(1H-indol-3-yl)-4-[2-(4-methyl-piperazin-1-yl)-quinazolin-4-yl]-1H-pyrrole-2,5-dione (hereafter, referred to as ("COMPOUND A") as a protein kinase C inhibitor. COMPOUND A is a protein kinase C (PKC) inhibitor compound of Formula I

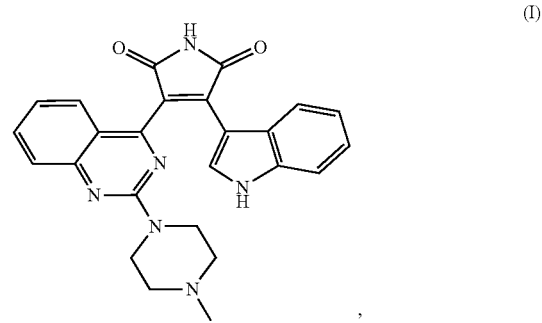 [SMILES: CN1CCN(c2nc(C3=C(c4c[nH]c5ccccc45)C(=O)NC3=O)c3ccccc3n2)CC1]

COMPOUND A is described in WO02/38561 and U.S. Pat. No. 6,645,970, The synthesis of COMPOUND A and its acetate salt is described at Example 56 of WO WO02/38561, which is hereby incorporated by reference in its entirety.

When referring to COMPOUND A, the term "salt" or "salts" is understood to be a salt of COMPOUND A that can be present alone or in mixture with the free compound of Formula (I) and are preferably pharmaceutically acceptable salts. Such salts are formed, for example, as acid addition salts, preferably with organic or inorganic acids, from the compound of Formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as acetic acid, fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient. The salts of COMPOUND A are preferably pharmaceutically acceptable salts; suitable counter-ions forming pharmaceutically acceptable salts are known in the field. A most preferred salt of the COMPOUND A is the acetate salt.

Pharmaceutical combinations of the present invention may include a MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof.

The MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) is a compound of formula (II)

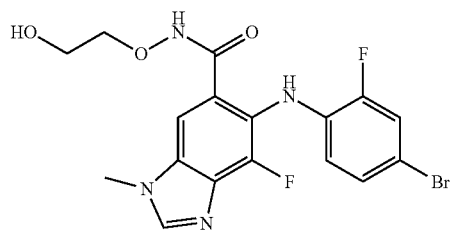

(II)

The MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) is described in PCT Application No. WO 03/077914, and methods for its preparation have been described, for example, in Example 18 therein.

Except as herein disclosed, the compounds used in the present invention may possess one or more asymmetric centers and can be produced as individual (R)- or (S)-stereoisomers or as mixtures thereof as described in PCT Application No. WO03/077914. Except as otherwise indicated, the description or naming of a particular compound in the specification and claims is intended to include both individual enantiomers, diastereomeric mixtures, racemic or otherwise, thereof. Accordingly, this invention also includes all such isomers, including diasteroemeric mixtures ad resolved enantiomers of the compounds of this invention. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced organic Chemistry", $4^{th}$ edition, J. March. John Wiley and Sons, New York, 1992).

The MEK inhibitor compound (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) is a compound of formula (III)

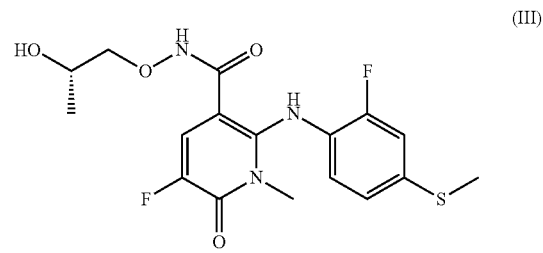 [SMILES: CSc1ccc(Nc2c(C(=O)NOC[C@H](C)O)cc(F)c(=O)n2C)c(F)c1]

(III)

The MEK inhibitor compound (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) is described in Example 25-BB of PCT Application No. WO2007/044084, and methods for its preparation have been described therein.

Additional MEK inhibitors that may be used in the combination of the present invention include, but are not limited to, PD0325901 (Pfizer)(See PCT Publication No. WO02/06213), PD-184352 (Pfizer), RDEA119 (Ardea Biosciences), GSK1120212 (GlaxoSmithKline)(See PCT Publication No. WO05/121142), XL518 (Exelexis), AS-701255 (Merck Serono), AS-701173 (Merck Serono), AS703026 (Merck Serono), RDEA436 (Ardea Biosciences, E6201 (Eisai) (See Goto et al, Journal of Pharmacology and Experimental Therapeutics, 3331(2): 485-495 (2009)), RO4987655 (Hoffmann-La Roche), JTP-74057, RG7167, and/or RG7420.

Preferably, the MEK inhibitor compound used in the combination of the present invention is selected from the group consisting of 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), or a pharmaceutically acceptable salt thereof.

A MEK inhibitor compound useful in the present combination is also PD0325901 N-[2(R),3-Dihydroxypropoxy]-3,4-difluoro-2-(2-fluoro-4-iodophenylamino)benzamide (See PCT Publication No. WO02/06213).

Preferably, the MEK inhibitor compound used in the combination of the present invention is 6-(4-bromo-2-fluorophenylamino)-7-fluoro-3-methyl-3H-benzoimidazole-5-carboxylic acid (2-hydroxyethoxy)-amide (COMPOUND B) or a pharmaceutically acceptable salt thereof.

As related to the MEK inhibitors, the term "salt" or "salts", unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Since a single compound of the present invention may include more than one acidic or basic moieties, the compounds of the present invention may include mono, di or tri-salts in a single compound.

In the case of an acidic moiety in a compound of the present invention, a salt may be formed by treatment of a compound of the present invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of the present invention.

With respect to basic moieties, a salt is formed by the treatment of a compound of the present invention with an acidic compound, particularly an inorganic acid. Preferred inorganic salts of this type may include, for example, the hydrochloric, hydrobromic, sulfuric, phosphoric or the like salts. Preferred organic salts of this type, may include, for example, salts formed with acetic, succinic, citric, maleic, fumaric, D-glutamic, glycolic, benzoic, cinnamic and the like organic acids. An especially preferred salt of this type is a hydrochloride or sulfate salt of COMPOUND B of the present invention.

Additional pharmaceutically acceptable salts of COMPOUND B and COMPOUND C suitable for the present invention include the salts disclosed in PCT Application No. WO 03/077914 and PCT Application No. WO2007/044084, which are both hereby incorporated into the present application by reference.

Unless otherwise specified, or clearly indicated by the text, reference to therapeutic agents useful in the pharmaceutical combination of the present invention includes both the free base of the compounds, and all pharmaceutically acceptable salts of the compounds.

The structure of the compounds identified by code nos., generic or trade names may be taken from the actual edition of the standard compendium "The Merck Index" or from databases, e.g., Patents International (IMS World Publications). The corresponding content thereof is hereby incorporated by reference.

In each case where citations of patent applications are given above, the subject matter relating to the compounds is hereby incorporated into the present application by reference. The compounds used as therapeutic agents in the pharmaceutical combinations of the present invention can be prepared and administered as described in the cited documents, respectively. Also within the scope of this invention is the combination of two separate therapeutic agents as set forth above, i.e., a pharmaceutical combination within the scope of this invention could include three therapeutic agents or more.

A pharmaceutical combination which comprises (a) a PKC inhibitor compound, or a pharmaceutically acceptable salt thereof, and (b) at least one MEK inhibitor compound, or a pharmaceutically acceptable salt thereof, and optionally a pharmaceutically acceptable carrier, will be referred to hereinafter as a COMBINATION OF THE INVENTION. This term is also taken to mean a pharmaceutical combination which consists of (a) a PKC inhibitor compound, or a pharmaceutically acceptable salt thereof, and (b) one MEK inhibitor compound, or a pharmaceutically acceptable salt thereof, and optionally a pharmaceutically acceptable carrier, wherein the PKC inhibitor and the MEK inhibitor compound are the sole therapeutic agents.

An example of a COMBINATION OF THE INVENTION is a pharmaceutical combination which comprises (a) a PKC inhibitor compound 3-(1H-indol-3-yl)-4-[2-(4-methyl-piperazin-1-yl)-quinazolin-4-yl]-1H-pyrrole-2,5-dione (COMPOUND A), or a pharmaceutically acceptable salt thereof, and (b) at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally a pharmaceutically acceptable carrier.

In a preferred embodiment of the present invention, the combination partners are (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound selected from the group consisting of 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C) or a pharmaceutically acceptable salt thereof.

In another preferred embodiment of the present invention, the combination partners are (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound 6-(4-bromo-2-fluorophenylamino)-7-fluoro-3-methyl-3H-benzoimidazole-5-carboxylic acid (2-hydroxyethoxy)-amide (COMPOUND B) or a pharmaceutically acceptable salt thereof.

In a preferred embodiment of the present invention, the combination partners are (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound (S)-5-fluoro-2-(2-fluoro-4-(methylthio) phenylamino)-N-(2-hydroxypropoxy)-1-methyl-6-oxo-1,6-dihydropyridine-3-carboxamide (COMPOUND C), or a pharmaceutically acceptable salt thereof.

The present invention also pertains to a combined preparation or a pharmaceutical composition comprising (a) a PKC inhibitor compound, e.g. 3-(1H-indol-3-yl)-4-[2-(4-methyl-piperazin-1-yl)-quinazolin-4-yl]-1H-pyrrole-2,5-dione (COMPOUND A), or a pharmaceutically acceptable salt thereof, and (b) a MEK inhibitor selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, and optionally a pharmaceutically acceptable carrier.

In one embodiment, the present invention relates to a combined preparation which comprises: (i) one or more unit dosage forms of combination partner (a), and (ii) one or more unit dosage forms of combination partner (b).

The present invention particularly pertains to a COMBINATION OF THE INVENTION useful for treating or preventing a proliferative disease in a subject in need thereof. In this embodiment of the present invention, the COMBINATION OF THE INVENTION is used for the treatment or prevention of a proliferative disease comprising administering to the subject a combination therapy, comprising an effective amount of a PKC inhibitor, e.g. 3-(1H-indol-3-yl)-4-[2-(4-methyl-piperazin-1-yl)-quinazolin-4-yl]-1H-pyrrole-2,5-dione (COMPOUND A), or a pharmaceutically acceptable salt thereof, and a MEK inhibitor compound, e.g. which is selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof. Preferably, the MEK inhibitor compound is administered at therapeutically effective dosages which, when combined, provide a beneficial effect. The administration may be simultaneous or sequential.

The proliferative disease treated or prevented by the COMBINATION OF THE INVENTION is mainly tumor and/or cancer. Examples of proliferative diseases include melanoma, in particular uveal melanoma, metastatic uveal melanoma, GNAQ or GNA11 mutant uveal melanoma and cancer, and more particularly uveal melanoma, metastatic uveal melanoma, and GNAQ or GNA11 mutant metastatic uveal melanoma.

In a one embodiment of the present invention, the proliferative disease is a solid tumor. The term "solid tumor" especially means melanoma, in particular uveal melanoma, e.g. metastatic uveal melanoma. Furthermore, depending on the tumor type and the particular combination used a decrease of the tumor volume can be obtained. The combinations disclosed herein are also suited to prevent the metastatic spread of tumors and the growth or development of micrometastases. The combinations disclosed herein are in particular suitable for the treatment of poor prognosis patients, especially such poor prognosis patients having metastatic uveal melanoma.

In a further embodiment, the proliferative disease is melanoma, in particular uveal melanoma, e.g. metastatic uveal melanoma.

In a further embodiment, the proliferative disease is uveal melanoma, e.g. metastatic uveal melanoma.

It will be understood that the COMBINATION OF THE INVENTION may be used solely for the treatment of a proliferative disease in accordance with the present invention.

It has been found that the combination therapy comprising the COMBINATION OF THE INVENTION results in unexpected improvement in the treatment or prevention of proliferative diseases as compared to the monotherapy. When administered simultaneously, sequentially or separately, the PKC inhibitor compound 3-(1H-indol-3-yl)-4-[2-(4-methyl-piperazin-1-yl)-quinazolin-4-yl]-1H-pyrrole-2,5-dione (COMPOUND A) and the MEK inhibitor compound 6-(4-bromo-2-fluorophenylamino)-7-fluoro-3-methyl-3H-benzo-imidazole-5-carboxylic acid (2-hydroxyethoxy)-amide, (COMPOUND B) interact synergistically to inhibit cell proliferation.

The nature of proliferative diseases is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically therapeutic agents used in the combination of the invention.

A further benefit is that lower doses of the therapeutic agents of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are in particular, for example, open label, dose escalation studies in patients with a proliferative diseases. Such studies prove in particular the synergism of the therapeutic agents of the COMBINATION OF THE INVENTION. The beneficial effects on proliferative diseases may be determined directly through the results of these studies which are known as such to a person skilled in the art. Such studies may be, in particular, be suitable to compare the effects of a monotherapy using either therapeutic agent and a COMBINATION OF THE INVENTION.

In one embodiment, the dose of the PKC inhibitor COMPOUND A is escalated until the Maximum Tolerated Dosage is reached, and a MEK inhibitor compound of the present invention is administered with a fixed dose. Alternatively, the PKC inhibitor COMPOUND A may be administered in a fixed dose and the dose of at least MEK inhibitor of the present invention may be escalated. Each patient may receive doses of the PKC inhibitor COMPOUND A and/or a MEK inhibitor of the present invention either daily or intermittently. The efficacy of the treatment may be determined in such studies, e.g., after 12, 18 or 24 weeks by evaluation of symptom scores, e.g. every 6 weeks.

In a preferred embodiment, the MEK inhibitor is COMPOUND B or a pharmaceutically acceptable salt thereof. In a preferred embodiment, the MEK inhibitor is COMPOUND B.

In a preferred embodiment, the MEK inhibitor is COMPOUND C, or a pharmaceutically acceptable salt thereof.

Determining a synergistic interaction between one or more components, the optimum range for the effect and absolute dose ranges of each component for the effect may be definitively measured by administration of the components over different w/w ratio ranges and doses to patients in need of treatment.

In a preferred embodiment of the present invention, the COMBINATION OF THE INVENTION comprises a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and a MEK inhibitor compound selected from the group comprising 6-(4-bromo-2-fluorophenylamino)-7-fluoro-3-methyl-3H-benzoimidazole-5-carboxylic acid (2-hydroxy-ethoxy)-amide (COMPOUND B), (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C), PD0325901, PD-184352, RDEA119, GSK1120212, XL518, AS-701255, AS-701173, AS703026, RDEA436, E6201, RO4987655, JTP-74057, RG7167, and/or RG7420 or a pharmaceutically acceptable salt thereof, for use in the treatment or prevention of a proliferative disease, e.g. uveal melanoma, metastatic uveal melanoma, and GNAQ or GNA11 mutant uveal melanoma, preferably uveal melanoma harboring mutations in either GNAQ or GNA11.

In one aspect, the present invention provides a synergistic combination for human administration comprising (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound of the present invention, preferably COMPOUND B, or a pharmaceutically acceptable salt thereof, in a combination range (w/w) which corresponds to the ranges observed in a tumor model, e.g., as described in the Examples below, used to identify a synergistic interaction.

In another aspect, the present invention provides a synergistic combination for human administration comprising (a) a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound of the present invention, preferably COMPOUND B, or a pharmaceutically acceptable salt thereof, in a combination range (w/w) which corresponds to the ranges observed in a tumor model, e.g., as described in the Examples below, used to identify a synergistic interaction.

According to a further aspect, the present invention provides a synergistic combination for administration to humans comprising (a) a PKC inhibitor 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) a MEK inhibitor compound of the present invention, preferably COMPOUND B, or a pharmaceutically acceptable salt thereof, where the dose range of each component corresponds to the synergistic ranges observed in a suitable tumor model, e.g., the tumor models described in the Examples below, primarily used to identify a synergistic interaction.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be either administered in a single formulation or unit dosage form, administered concurrently but separately, or administered sequentially by any suitable route. The unit dosage form may also be a fixed combination.

The pharmaceutical compositions for separate administration of both combination partners, or for the administration in a fixed combination, i.e. a single galenical composition comprising the COMBINATION OF THE INVENTION, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers, especially suitable for enteral or parenteral application.

The novel pharmaceutical composition contains may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See *The Handbook of Pharmaceutical Excipients*, 4th edition, Rowe et al., Eds., American Pharmaceuticals Association (2003); and *Remington: the Science and Practice of Pharmacy*, 20th edition, Gennaro, Ed., Lippincott Williams & Wilkins (2003).

These optional additional conventional carriers may be incorporated into the oral dosage form either by incorporating the one or more conventional carriers into the initial mixture before or during granulation or by combining the one or more conventional carriers with granules comprising the combination of agents or individual agents of the combination of agents in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In one embodiment, the present invention also pertains to a COMBINATION OF THE INVENTION for use in the preparation of a pharmaceutical composition or medicament for the treatment or prevention of a proliferative disease in a subject in need thereof.

In a further embodiment, the present invention pertains to the use of a PKC inhibitor compound 3-(1H-indol-3-yl)-4-[2-(4-methyl-piperazin-1-yl)-quinazolin-4-yl]-1H-pyrrole-2,5-dione (COMPOUND A) or a pharmaceutically acceptable salt thereof, and (b) at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, for the preparation of a pharmaceutical composition or medicament for the treatment or prevention of a proliferative disease in a subject in need thereof. Preferred is a MEK inhibitor selected from 6-(4-bromo-2-fluorophenylamino)-7-fluoro-3-methyl-3H-benzoimidazole-5-carboxylic acid (2-hydroxyethoxy)-amide (COMPOUND B) or (S)-5-fluoro-2-(2-fluoro-4-(methylthio)phenylamino)-N-(2-hydroxypropoxy)-1-methyl-6-oxo-1,6-dihydropyridine-3-carboxamide (COMPOUND C).

In accordance with the present invention, a therapeutically effective amount of each of the combination partner of the COMBINATION OF THE INVENTION may be administered simultaneously or sequentially and in any order, and the components may be administered separately or as a fixed combination. For example, the method of treating a proliferative disease according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the COMBINATION OF THE INVENTION may be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the combination partners (a) and (b) of the COMBINATION OF THE INVENTION that yield efficacy without toxicity are based on the kinetics of the therapeutic agents' availability to target sites, and may be determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The PKC inhibitor compound COMPOUND A may administered to a suitable subject daily in single or divided doses at an effective dosage in the range of about 0.05 to about 50 mg per kg body weight per day, preferably about 0.1-25 mg/kg/day, more preferably from about 0.5-10 mg/kg/day, in single or divided doses. For a 70 kg human, this would amount to a preferable dosage range of about 35-700 mg per day.

The MEK inhibitor compound COMPOUND B may be administered to a suitable subject daily in single or divided doses at an effective dosage in the range of about 0.001 to about 100 mg per kg body weight per day, preferably about 1 to about 35 mg/kg/day, in single or divided doses. For a 70 kg human, this would amount to a preferable dosage range of about 0.05 to 7 g/day, preferably about 0.05 to about 2.5 g/day.

The MEK inhibitor compound COMPOUND C may be administered daily to a suitable subject in single or divided doses at an effective dosage in the range of about 0.001 to about 100 mg per kg body weight per day, preferably about 1 mg/kg/day to about 35 mg/kg/day, in single or divided doses. For a 70 kg human, this would amount to a preferable dosage range of about 0.07 to 2.45 g/day, preferably about 0.05 to about 1.0 g/day.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The present invention relates to a method of treating a subject having a proliferative disease comprising administered to said subject a COMBINATION OF THE INVENTION in a quantity, which is jointly therapeutically effective against a proliferative disease. In particular, the proliferative disease to be treated with a COMBINATION OF THE INVENTION is selected from melanoma, uveal melanoma, metastatic uveal melanoma, GNAQ or GNA11 mutant uveal melanoma and GNAQ or GNA11 mutant metastatic uveal melanoma.

Furthermore, the treatment can comprise surgery or radiotherapy.

The present invention further relates to the COMBINATION OF THE INVENTION for use in the treatment of a proliferative disease, particularly cancer, such as uveal melanoma, metastatic uveal melanoma, GNAQ or GNA11 mutant uveal melanoma and cancer, and more particularly uveal melanoma, metastatic uveal melanoma, and GNAQ or GNA11 mutant metastatic uveal melanoma.

The present invention further provides a commercial package comprising as therapeutic agents COMBINATION OF THE INVENTION, together with instructions for simultaneous, separate or sequential administration thereof for use in the delay of progression or treatment of a proliferative disease in a subject in need thereof.

The following Examples illustrate the invention described above; they are not, however, intended to limit the scope of the invention in any way. The beneficial effects of the pharmaceutical combination of the present invention can also be determined by other test models known as such to the person skilled in the pertinent art.

EXAMPLES

Example 1

Cell Lines and Cell Culture 92.1 and OMM-1 uveal melanoma cell lines were cultured in Roswell Park Memorial Institute medium (RPMI 1640) (American Type Culture Collection (ATCC #30-2001)) supplemented with 10% fetal bovine serum and incubated at 37° C./5% carbon dioxide. The 92.1 cell line possess a GNAQ mutation, and the OMM1 cell line harbors a mutation in GNA11.

Compound Preparation for In Vitro Experimentation

Compound stocks of 3-(1H-indol-3-yl)-4-[2-(4-methyl-piperazin-1-yl)-quinazolin-4-yl]-1H-pyrrole-2,5-dione, hereafter AEB071, and of 6-(4-bromo-2-fluorophenylamino)-7-fluoro-3-methyl-3H-benzoimidazole-5-carboxylic acid (2-hydroxyethoxy)-amide, hereafter COMPOUND B, were prepared in dimethylsulfoxide (DMSO) at a final concentration of 10 mM.

Proliferation Measurement by xCELLigence

Growth of uveal cells was continuously monitored with the xCELLigence real-time cell analyzer. E-plates (Roche #05 232 368 001) were incubated with cells added at a final concentration of 3000 cells per 100 µl per well. Impedance was measured every 2 hours for 24 hours. After 24 hours, DMSO, COMPOUND B, AEB071 or both compounds were added to the wells at a final concentration of 1 µM per compound to a total volume of 120 µl. Impedance was measured every 2 hours over 7 days. Data was normalized to day 0 prior to compound addition.

The effect of 3-(1H-indol-3-yl)-4-[2-(4-methyl-piperazin-1-yl)-quinazolin-4-yl]-1H-pyrrole-2,5-dione (COMPOUND A) and 6-(4-bromo-2-fluorophenylamino)-7-fluoro-3-methyl-3H-benzoimidazole-5-carboxylic acid (2-hydroxyethoxy)-amide (COMPOUND B) on uveal melanoma proliferation in vitro is shown (FIG. 1). The growth of uveal melanoma cell lines over the course of 6 days was measured by xCELLigence technology in the presence of 0.5 µM DMSO, 0.5 µM AEB071, 0.5 µM COMPOUND B or 0.5 µM AEB071+0.5 µM COMPOUND B. In the 92.1 and OMM1 cell lines which possess GNAQ and GNA11 mutations respectively, AEB071 delayed cell growth; this effect was exacerbated when in combination with COMPOUND B. COMPOUND B as a single agent had a modest effect on the growth of both uveal melanoma cell lines 92.1 and OMM1; it was quite striking that the combination of the two agents was able to fully suppress proliferation of both cell lines.

Example 2

Cell Lines and Cell Culture

As per Example 1
Compound Preparation for In Vitro Experimentation
As per Example 1.
Cell Proliferation in Combination Dose Matrix Cells were seeded at a density of 3000 cells per 100 µl of medium per well in 96-well plates (Costar #3904) and incubated overnight prior to compound addition. Compound stock was freshly prepared in the appropriate culture medium and manually added to the plates by electronic multichannel pipette in three replicates. Cells were treated with compound alone or with a combination of AEB071 and COMPOUND B diluted 1:2 for a ten point dilution ranging from 0.039 µM to 10 µM. The viability of cells was assessed at the time of compound addition and after 144 hours of treatment by quantification of cellular ATP levels via Cell Titer Glo (Promega #G7571) according to the manufacturer's protocol. Plates were read on a luminescence plate reader (Victor X4, Perkin Elmer). Fractional inhibition of growth was calculated using XLfit and normalized to no compound wells. For growth inhibition, day 0 values were subtracted before calculating inhibition. Data was analyzed by Chalice software (http://chalice.zalicus.com/documentation/analyzer/index.jsp) to calculate growth inhibition, inhibition and HSA excess.

Results

Figure 2A:
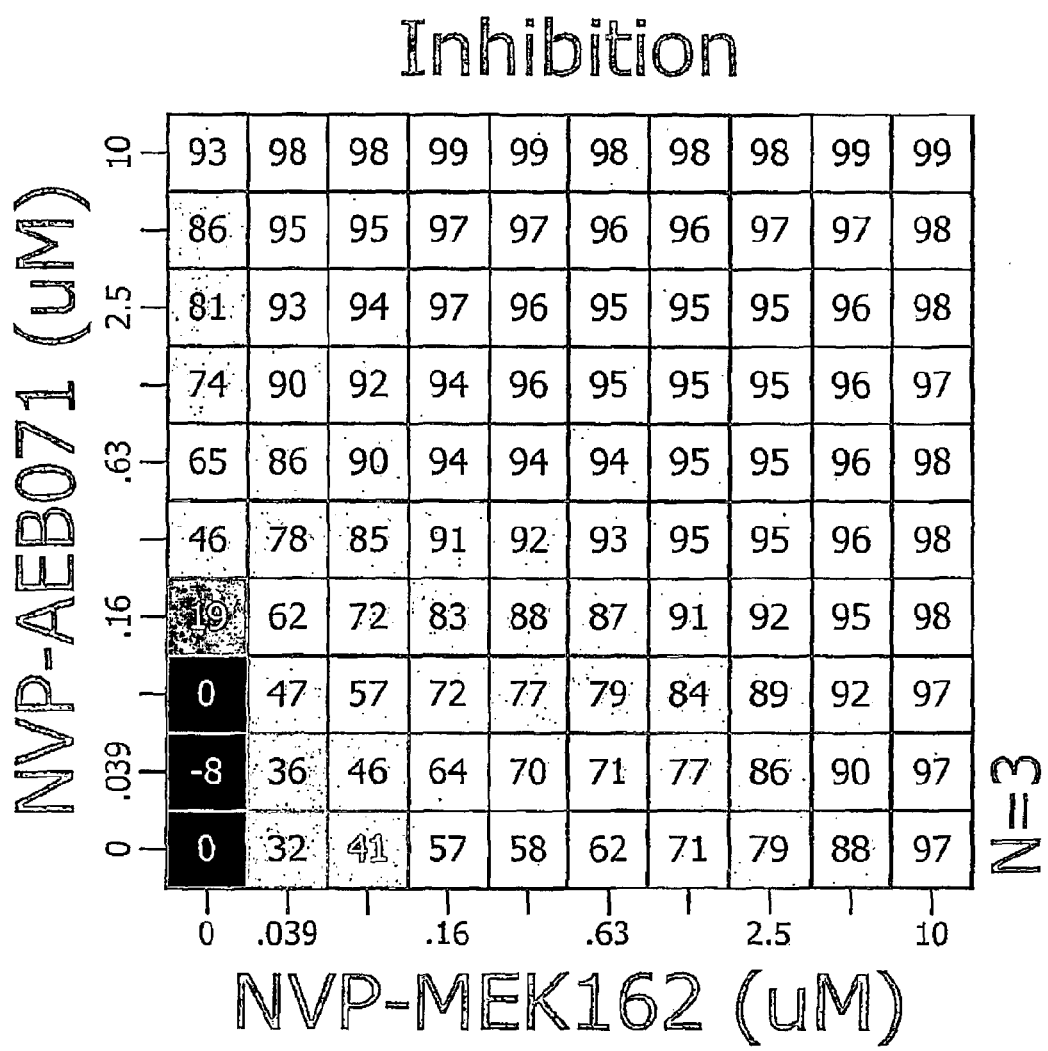
FIG. 2 shows a closer look at the pattern of synergy between the AEB071 and COMPOUND B in the 92.1 uveal melanoma cell line, and displays the synergistic effect between the two agents. The dose matrix between the two agents is shown; the effect on cell growth relative to untreated cells is shown in the top side panel, the excess inhibition in the center panel and the growth inhibition relative to day zero normalization is shown in the bottom panel. Both single agent COMPOUND B and AEB071 were active in 92.1, but importantly, combining the two agents yielded more than additive magnitudes of response at lower doses, indicating the combination of both agents together is more effective at inhibiting proliferation of uveal melanoma cell line 92.1 in vitro than either single agent alone.
Figure 2B:
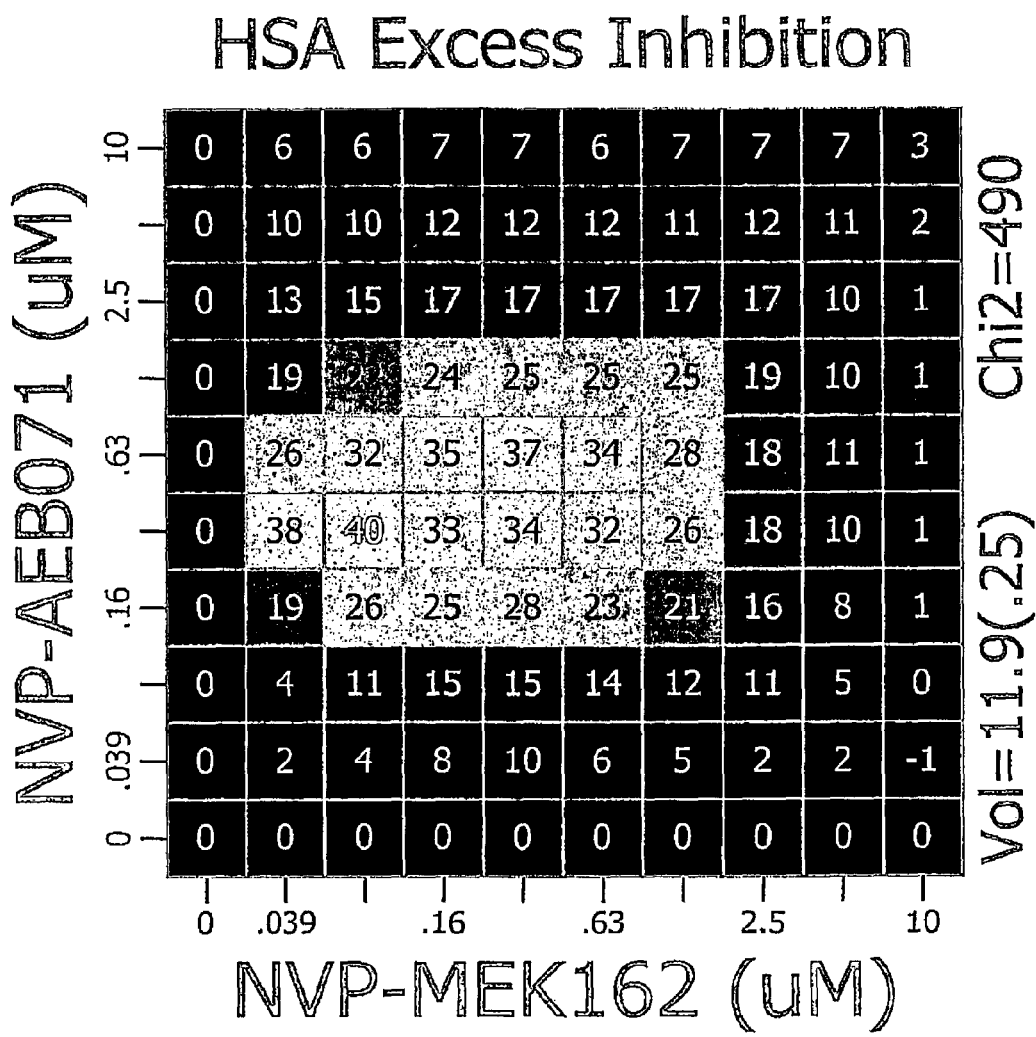
Figure 2C:
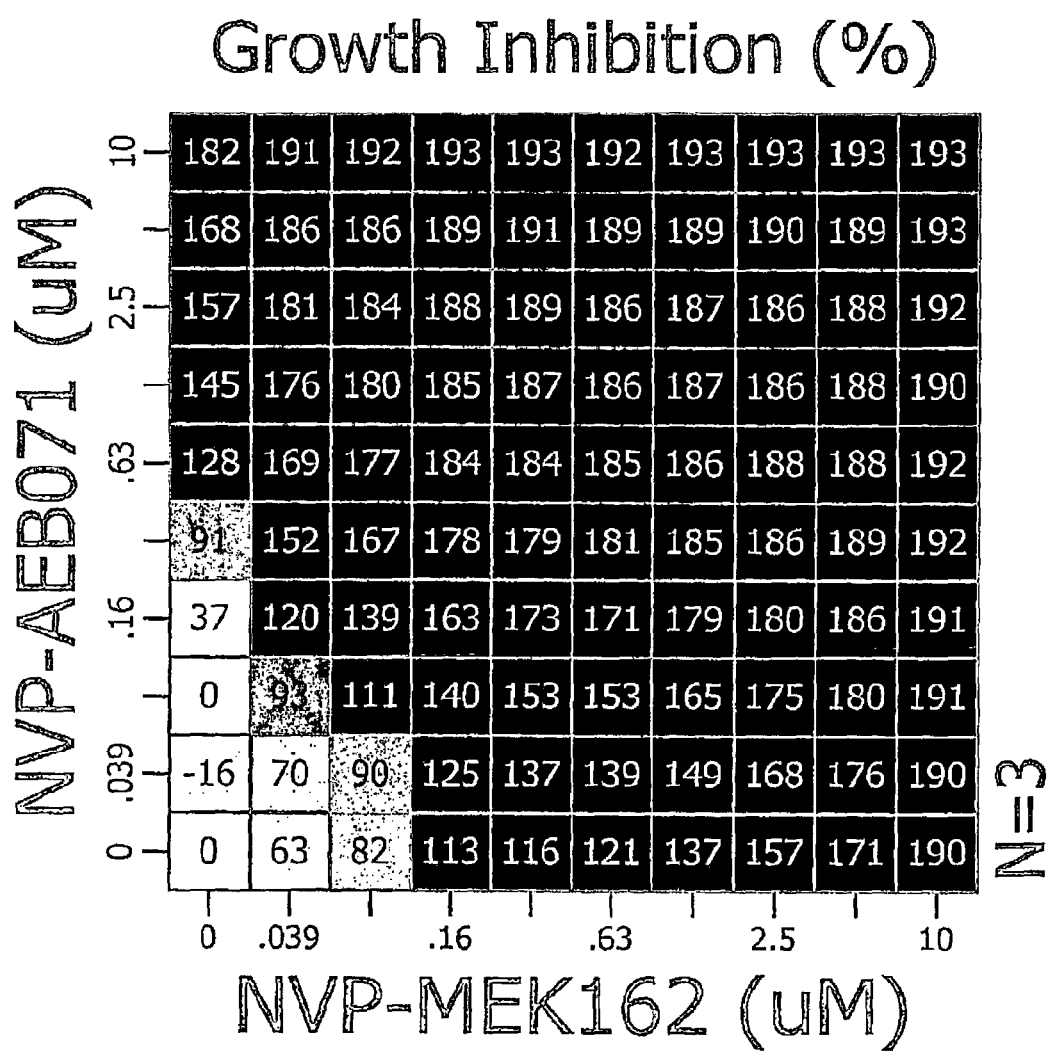

The anti-proliferative effect of AEB071 in combination with COMPOUND B is due to synergy between the two agents, as demonstrated in FIG. 2. FIG. 2 provides a closer look at the patterns of synergy between the two agents in the 92.1 cell line. The dose matrix between the two agents is shown; the effect on cell growth relative to untreated cells is shown in the top panel, the excess inhibition (HSA) in the center panel and the growth inhibition relative to day zero normalization is shown in the bottom panel. Methods of calculations for growth inhibition, inhibition and HSA excess are known in the art.

Both single agents COMPOUND B and AEB071 were active in cell line 92.1, but importantly combining the two agents yielded more than additive magnitudes of response at lower doses. For example 0.16 µM of single agent COMPOUND B yielded a 57% growth inhibition, and single agent AEB071 at 0.16 µM gave 19% growth inhibitions, but the combination of the two agents at these does yielded a growth inhibition of 82% (FIG. 2, top panel). This dose combination represented an excess inhibition of 25 as seen in FIG. 2 middle panel. Inhibition and excess inhibition values for all dose combinations can be seen in FIG. 2. The growth rate of the cells during the 3 day assay was taken into account for the calculation of growth inhibition percent shown in FIG. 2, bottom panel. 100% indicated stasis, meaning the cells had neither grown nor died during the course of the assay, values in excess of 100 indicate death, 200 being complete cell death, and values below 100 indication growth from the start of the assay to the day 3 end point.

Example 3

Biochemical Profile by Protein Immunoblot Following Drug Treatment of Uveal Melanoma Cell Lines 92.1 and OMM1

Uveal melanoma cells were incubated with 0.5 µM AEB071, 0.5 µM COMPOUND B, both compounds or DMSO alone. Cells were lysed after 2, 4, 8, 24 or 48 hours of treatment in M-PER mammalian protein extraction buffer containing PhosStop Phosphatase inhibitor cocktail tablet (Roche Diagnostics #04 906 837 001) and Complete Protease Inhibitor cocktail tablet (Roche Diagnostics #11 836 145 001). Proteins were separated on a 4-12% Bis-Tris NuPAGE SDS gel (Invitrogen #WG1403Bx10) and subsequently transferred to a nitrocellulose membrane using a dry blotting system (Invitrogen iBLOT). Proteins were detected with 1:1000 dilutions of anti-p44/42 MAPK (Cell Signaling Technologies #4377), anti-pMARCKS (Cell Signaling Technologies #2741), anti-pMEK1/2 (Cell Signaling Technologies #9121) and anti-Beta Actin (Ambion#AM4202). Beta actin was detected using the appropriate secondary antibody and an infrared dye detection system (Odyssey IRDye, LI-COR) according to the manufacturer's protocol. All other proteins were detected using an anti-rabbit-HRP secondary antibody and developed with SuperSignal West Dura Chemiluminescent Substrate (Thermo Scientific #34076) on a Syngene imaging system.

Results

Figure 3:
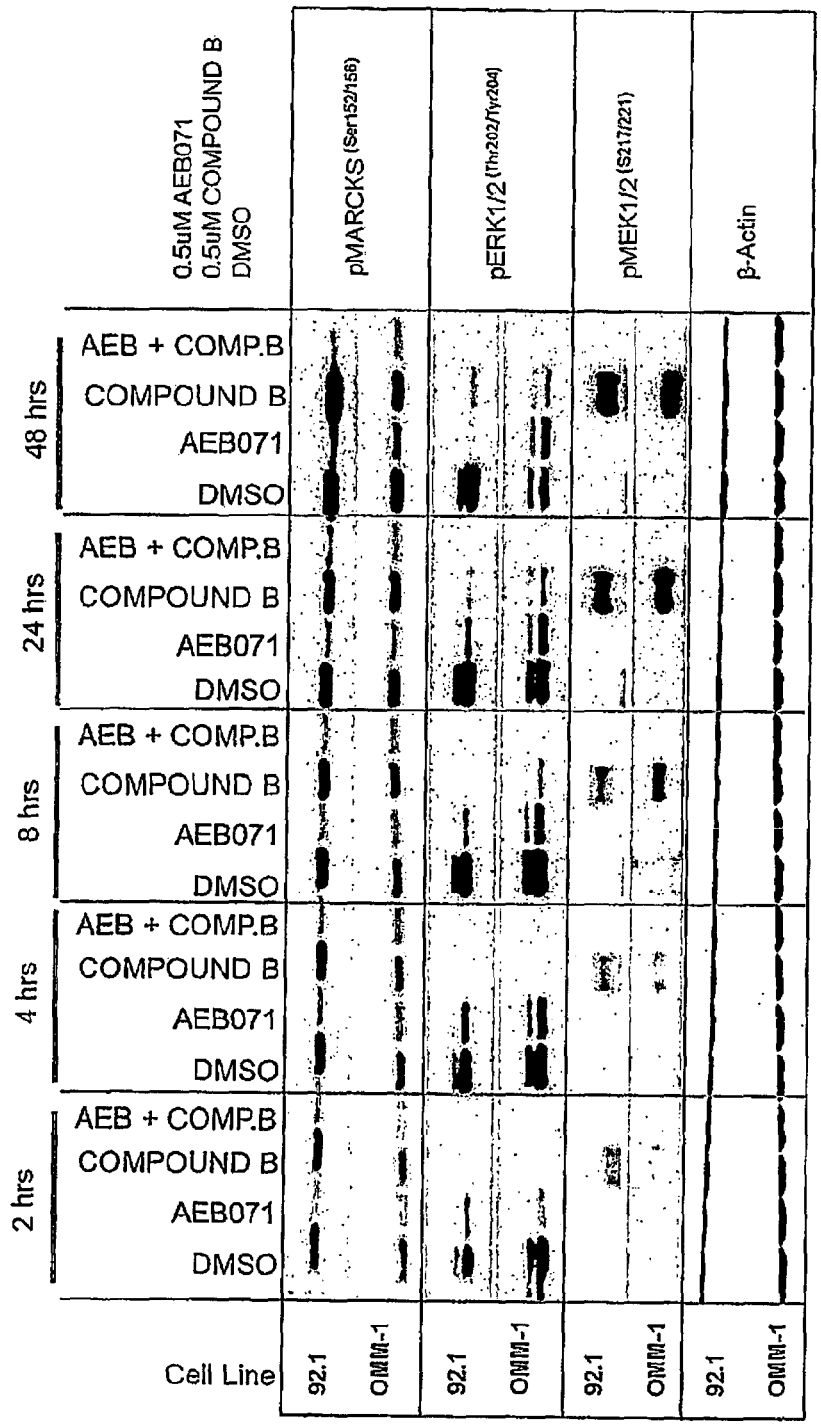
FIG. 3: The biochemical effect of these agents is assessed following treatment with 0.5 µM AEB071, 0.5 µM COMPOUND B or 0.5 µM of each agent together in the uveal melanoma cell lines 92.1 and OMM-1. The level of pMARCKS was attenuated. Addition of COMPOUND B to AEB071 had no further effect on pMARCKS expression. Treatment of the same cells with COMPOUND B led to a reduction in pERK1/2 levels, as could be seen at 2 hrs; by 24 hours, expression of pERK1/2 was beginning to return. Furthermore, single agent COMPOUND B treatment led to induction of pMEK1/2 expression over time in both cell lines; this was clearly observed following 48 hours of treatment. Surprisingly, only the combination of AEB071 and COMPOUND B yielded sustained suppression of pERK1/2, and pMEK1/2. Significantly, AEB071 clearly prevented pMEK induction caused by COMPOUND B single agent treatment. Thus, combination of AEB071 and COMPOUND B led to sustained phosphoprotein inhibition of pMEK, pERK and pMARCKS.

The biochemical effect of these agents was assessed following treatment with 0.5 µM AEBO071, 0.5 µM COMPOUND B or 0.5 µM of each agent together in the uveal melanoma cell lines 92.1 and OMM-1. The level of pMARCKS was attenuated (FIG. 3). Addition of COMPOUND B to AEB071 had no further effect on pMARCKS expression. Treatment of the same cells with COMPOUND B led to a reduction in pERK1/2 levels, as could be seen at 2 hrs, by 24 hours expression of pERK1/2 is beginning to return. Furthermore, single agent COMPOUND B treatment led to induction of pMEK1/2 expression over time in both cell lines; this was clearly observed following 48 hours of treatment. Surprisingly, only the combination of AEB071 and COMPOUND B yielded sustained suppression of pERK1/2, pMEK1/2. Significantly, AEB071 clearly prevented pMEK induction caused by COMPOUND B single agent treatment. The combination of AEB071 and COMPOUND B suppressed pathway components to a greater magnitude and duration compared to either single agent.

Figure 4:
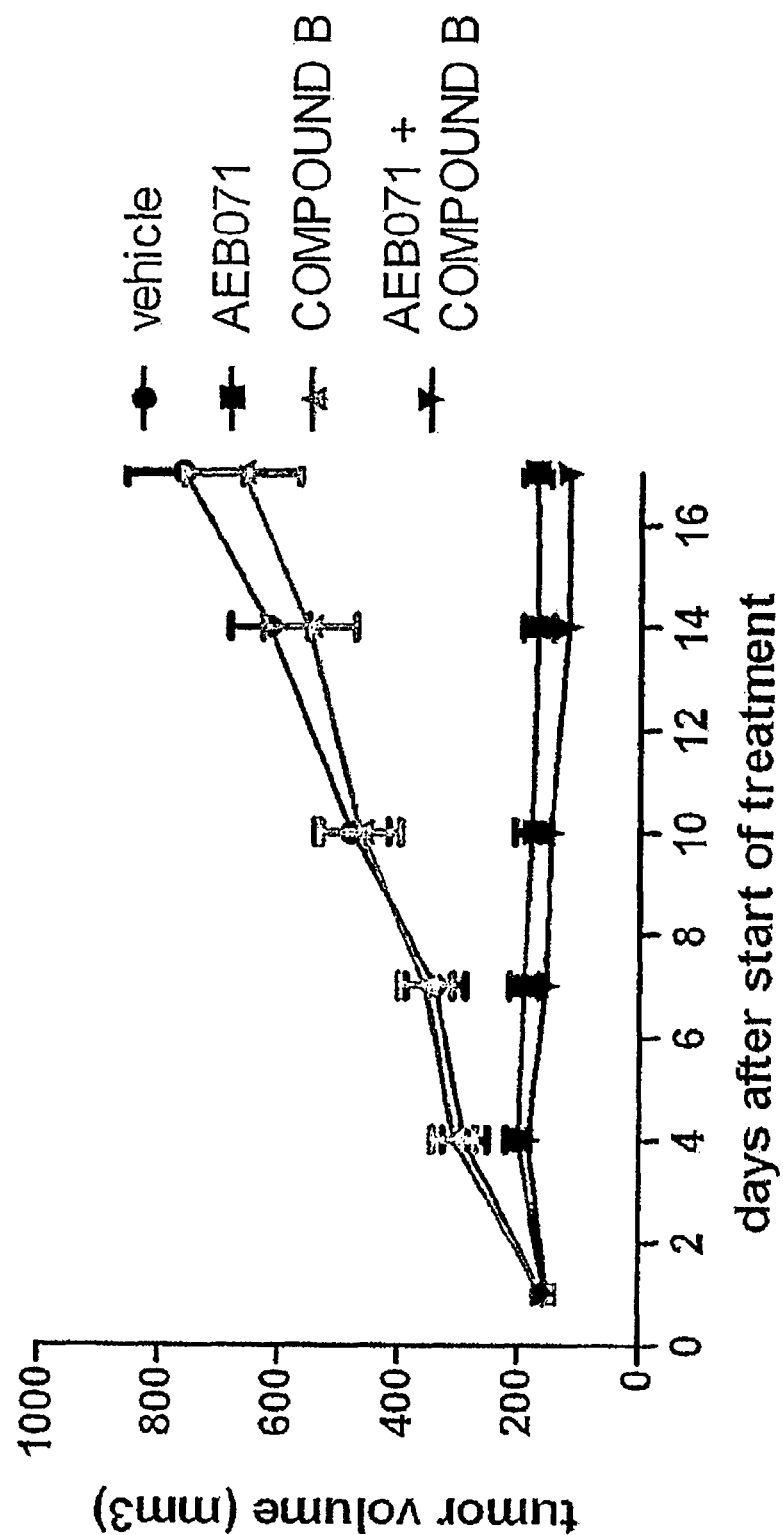
FIG. 4 shows the in vivo activity of AEB071 and COMPOUND B in the 92.1 human uveal melanoma nude mouse xenograft model. AEB071 was administered at 91 mg/kg three times daily dosing (TID) for 21 days. Efficacy was determined from tumor growth inhibition on day 17, the last day with all mice on the study. The activity was calculated at tumor/control (T/C), the percent mean tumor volume change from day 1 to day 17 in drug treated mice (ΔT) versus vehicle treated mice, or as a T/T0, the percent reduction in the group mean tumor volume from day 1.
Figure 6:
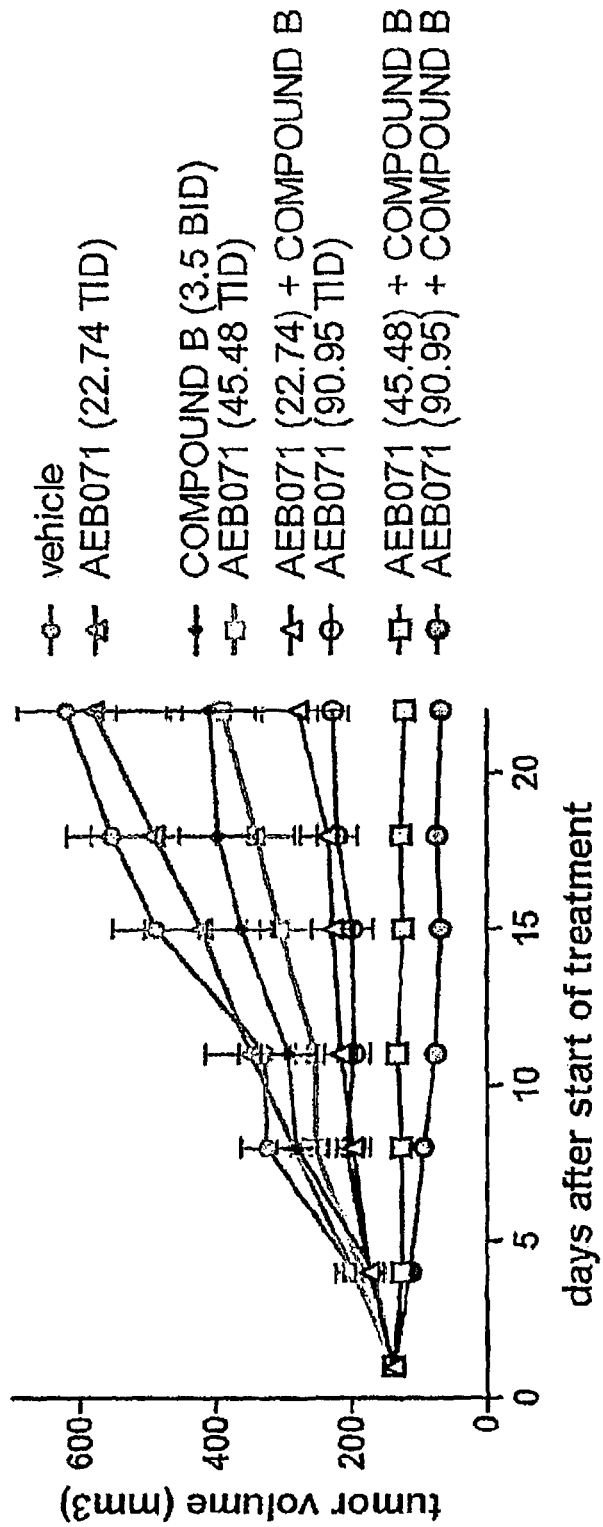
FIG. 6 shows the in vivo activity of AEB071 administered at 90.95, 45.58 and 22.74 mg/kg, (equivalent to 80, 40 and 20 mg/kg free base) with three times daily dosing (TID) for 21 days in combination with COMPOUND B at 3.5 mg/kg with twice daily dosing regimen in the 92.1 human uveal melanoma nude mouse xenograft model. Efficacy was determined from tumor growth inhibition on day 22. The activity was calculated at tumor/control (T/C), the percent mean tumor volume change from day 1 to day 22 in drug treated mice ($\Delta$T) versus vehicle treated mice, or as a T/T0, the percent reduction in the group mean tumor volume from day 1.

The 92.1 human uveal melanoma nude mouse xenograft model which possesses a GNAQ mutation was used to assess the in vivo activity of AEB071, COMPOUND B, and a combination of AEB071 and COMPOUND B as shown in Examples 4, 5 and 6. As can be seen from the results obtained, the in vitro synergy observed between COMPOUND B and AEB071 translated into in vivo efficacy. As shown in FIG. 4 monotherapy AEB071 treatment resulted in a 3% T/C (p<0.01), addition of COMPOUND B dosed twice daily at 3.5 mg/kg to the AEB071 regimen yielded a −22% T−T0 (p<0.001 median activity, but not significant compared to AEB071 alone). COMPOUND B had no activity in its own right with a T/C of 84%. The combination of the two compounds strongly prevented tumor growth in the uveal melanoma 92.1 model in vivo. Furthermore, treatment at multiple doses of AEB071 in combination with COMPOUND B was efficacious in 92.1 in vivo uveal melanoma model, as shown in FIG. 6. The effectiveness of the combination increased in a dose dependent manner, with increasing AEB071 dose in combination with COMPOUND B yielding a greater magnitude of response.

Example 4

Assessment of the In Vivo Activity in the 92.1 Human Uveal Melanoma Nude Mouse Xenograft Model Compound Preparation for In Vivo Experimentation
NVP-AEB071 (also referred to as AEB071) (acetate salt, 87.96% free base) powder was added to 20% polyethyleneglycol 400 (PEG400): 4.5% 0.1M HCl: 75.5% of 5% dextrose in water (D5W), designated as Vehicle 1, and stirred to obtain a clear red solution. NVP-COMPOUND B (also referred to as COMPOUND B) was formulated as a homogenous suspension in 1% carboxymethyl cellulose: 0.5% Tween® 80 in deionized water. A fresh suspension was prepared once per week for each compound and stored at 4° C.

Mice
Female athymic nude mice (Crl:NU(Ncr)-Foxn1nu, Charles River) were 9 weeks old, and had a body weight (BW) range of 20.6-26.9 g, on D1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-O'Cobs™ Laboratory Animal Bedding in static microisolators on a 12-hour light cycle at 20-22° C. (68-72° F.) and 40-60% humidity. DRS-NC specifically complies with the recommendations of the Guide for Care and Use of Laboratory Animals with respect to restraint, husbandry, surgical procedures, feed and fluid regulation, and veterinary care. The animal program at DRS-NC is accredited by the Association for Assessment and Accreditation of Laboratory Animal Care (AAALAC) International, which assures compliance with accepted standards for the care and use of laboratory animals.

Tumor Implantation and Measurement
The 92.1 uveal melanoma cells were harvested during exponential growth, and re-suspended in cold PBS (phosphate buffered saline) with 50% Matrigel™ (BD Biosciences). Each mouse was inoculated subcutaneously in the right flank with $5 \times 10^6$ cells (0.2 mL of cell suspension). Tumors were calipered in two dimensions to monitor growth as their mean volume approached the desired 100-150 $mm^3$ range. Tumor size, in $mm^3$, was calculated from:

$$\text{Tumor Volume} = (w^2 \times l)/2$$

where w=width and l=length, in mm, of the tumor. Tumor weight could be estimated with the assumption that 1 mg was equivalent to 1 $mm^3$ of tumor volume. Twelve days after tumor cell implantation, on Day 1 (D1) of the study, animals with individual tumor volumes of 108-256 $mm^3$ were sorted into six groups (n=10/group) with group mean tumor volumes of 153-159 $mm^3$.

AEB071 was administered at 91 mg/kg three times daily (TID) dosing for 21 days. Efficacy was determined from tumor growth inhibition on day 17, the last day with all mice on the study. The activity was calculated at tumor/control (T/C), the percent mean tumor volume change from day 1 to day 17 in drug treated mice (ΔT) versus vehicle treated mice, or as a T/T0, the percent reduction in the group mean tumor volume from day 1. As shown in FIG. 4, monotherapy AEB071 treatment resulted in a 3% T/C ($p<0.01$). Addition of COMPOUND B dosed twice daily at 3.5 mg/kg to the AEB071 regimen yielded a −22% T−T0 ($p<0.001$ median activity, but not significant compared to AEB071 alone). COMPOUND B had no activity in its own right with a T/C of 84%.

Example 5

Compound Preparation for In Vivo Experimentation

As per Example 4
Mice
As per Example 4
Tumor Implantation and Measurement
As per Example 4

Example 6

Compound Preparation for In Vivo Experimentation

As per Example 4
Mice
As per Example 4
Tumor Implantation and Measurement
As per Example 4

AEB071 monotherapy produced near complete mean tumor stasis during the dosing period whilst the combination caused modest mean tumor reduction. For two weeks following the dosing period tumors progressed at the control pace in AEB071 monotherapy treatment groups, whereas tumors progressed more slowly in the combination group (FIG. 5).

Figure 5:
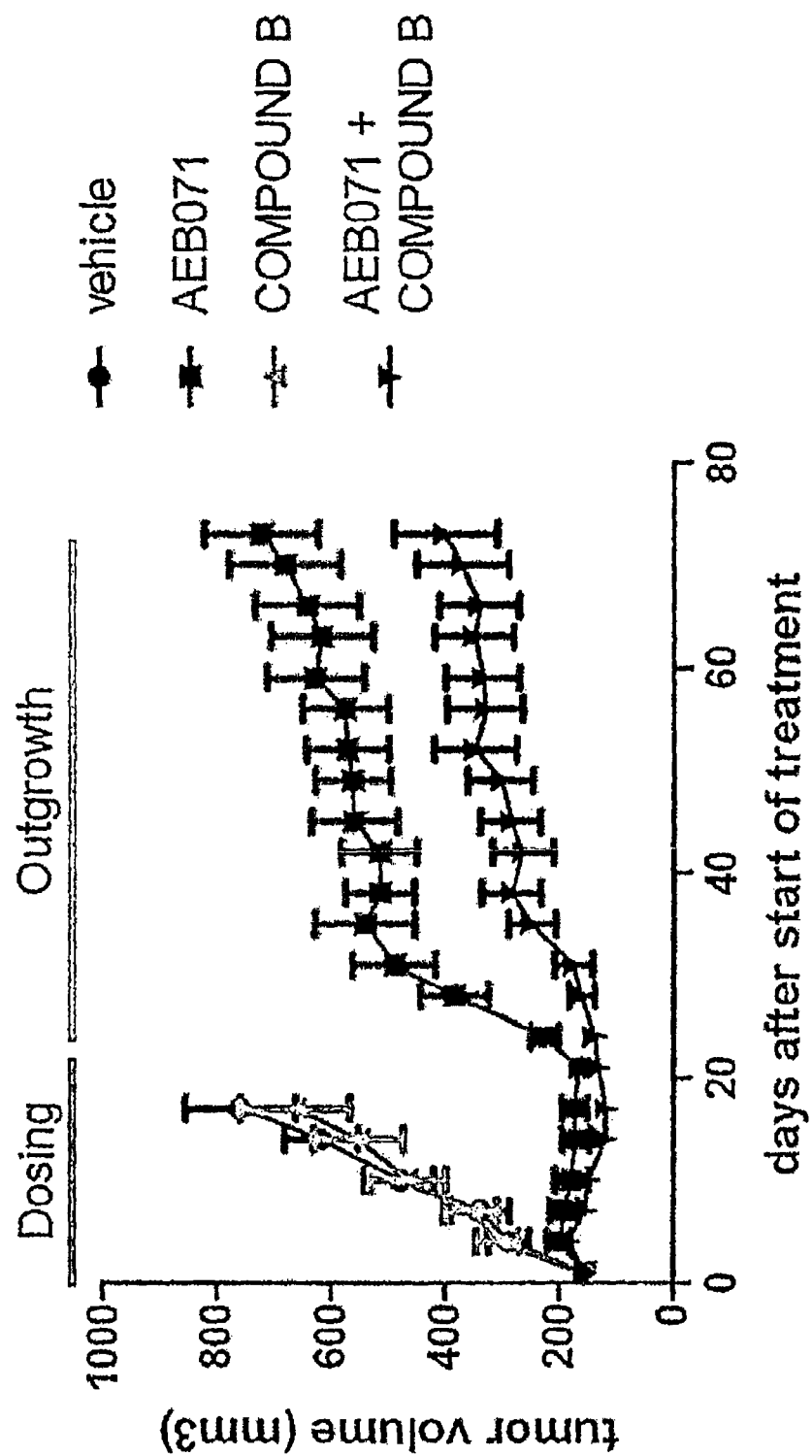
FIG. 5 shows tumor growth in vivo in the 92.1 human uveal melanoma nude mouse xenograft model followed for >70 days. Mice were dosed for 21 days, then treatment ceased and tumor outgrowth was monitored. Two weeks following the dosing period tumors progressed at the control pace in AEB071 monotherapy treatment groups, whereas tumors progressed at a slower rate in the combination group. Tumor growth delay was not calculated because two or more tumors per group became static after an initial growth period, but the trend of tumor outgrowth rate indicated the AEB071 plus COMPOUND B combination tumors grew out slower than AEB071 single agent. COMPOUND B single agent treated tumors were not monitored due to lack of efficacy. The data indicated that the combination of AEB071 with COMPOUND B has greater magnitude and duration of response compared to either single agent in the 92.1 in vivo model of uveal melanoma.

FIG. 5 shows tumor growth in vivo in the 92.1 human uveal melanoma nude mouse xenograft model followed for >70 days. Mice were dosed for 21 days, then treatment ceased and tumor outgrowth was monitored. Two weeks following the dosing period tumors progressed at the control pace in AEB071 monotherapy treatment groups, whereas tumors progressed at a slower rate in the combination group. Tumor growth delay was not calculated because two or more tumors per group became static after an initial growth period, but the trend of tumor outgrowth rate indicated the AEB071 plus COMPOUND B combination tumors grew out slower than AEB071 single agent, COMPOUND B single agent treated tumors were not monitored due to lack of efficacy. This data indicated the combination of AEB071 with COMPOUND B has a greater magnitude of response compared to either single agent in the in vivo 92.1 model of uveal melanoma.

FIG. 6 shows that treatment at multiple doses of AEB071 in combination with COMPOUND B was efficacious in a further in vivo study using the 92.1 uveal melanoma model. The effectiveness of the combination increased in a dose dependent manner, with increasing AEB071 dose in combination with COMPOUND B yielding a greater magnitude of response. AEB071 was administered at 90.95, 45.58 and 22.74 mg/kg, (equivalent to 80, 40 and 20 mg/kg free base) with three times daily dosing (TID) for 21 days in combination with COMPOUND B at 3.5 mg/kg with twice daily dosing in the 92.1 human uveal melanoma nude mouse xenograft model. Efficacy was determined from tumor growth inhibition on day 22. The activity was calculated at tumor/control (T/C), the percent mean tumor volume change from day 1 to day 22 in drug treated mice (ΔT) versus vehicle treated mice, or as a T/T0, the percent reduction in the group mean tumor volume from day 1. As shown in FIG. 6 monotherapy AEB071 at 90.95 mg/kg resulted in a 18% T/C (p<0.05). Monotherapy with 45.5 and 22.7 mg/kg resulted in 52% and 92% T/C respectively, and non-significant median inhibition. Addition of COMPOUND B dosed twice daily at 3./kg with AEB071 doses of 90.95 and 45.58 mg/kg yielded a −52% and −12% T−T0 respectively (p<0.001). COMPOUND B had no activity in its own right in this in vivo model with a T/C of 56%. The high dose combination yielded four partial regressions.

Conclusion

There is thus provided experimental evidence that combined PKC and MEK inhibition is synergistic and efficacious in uveal melanoma. This combination is thus beneficial in the setting of activating GNAQ or GNA11 mutations, since activating mutations in either gene lead to a dependency on PKC signaling. Combining these agents is antiproliferative in vitro and efficacious in vivo. PKC inhibition in uveal melanoma cell lines attenuates pMARCKS, but has a modest effect on pERK1/2 levels. Single agent MEK inhibition is able to block pERK1/2, however pMEK1/2 levels are induced over time with the MEK inhibitor leading to reactivation of pERK1/2. Only the combination of MEK and PKC inhibition is able to achieve sustained attenuated phosphorylation of MARCKS, ERK1/2 and MEK1/2.

Example 7

This is a multi-center, multinational, unblinded study of the combination of AEB071 and COMPOUND B. Eligible patients are patients diagnosed with metastatic uveal melanoma. There are two parts to the study. Phase 1b is a dose escalation study and the Phase II is a randomized two-arm, parallel-group evaluation of the MTD/RP2D {MTD (maximum tolerated dose)/RP2D (Recommended phase two dose)}obtained from Phase 1b. The study is designed to be open-label (unblinded) as all patients receive the same dose as other patients enrolled within the same dose cohort in the Phase Ib part of the study, and receive either the MTD/RP2D for the AEB071 and COMPOUND B combination BID (twice daily) or 45 mg COMPOUND B BID (twice daily) only in the Phase II study.

The investigational treatments under evaluation in the Phase Ib and Phase II consist of AEB071 and COMPOUND B or COMPOUND B as a single agent in the Phase II. The investigational treatments are administered as a flat-fixed dose, and not by body weight or body surface area.

All patients receive treatment daily on a 28-day schedule (a cycle), without interruption between cycles. Each patient may continue on treatment until they no longer derive benefit or experience significant adverse events, requiring withdrawal, discontinue at the discretion of the investigator, or withdraw consent.

The Phase Ib is a dose-escalation study designed to determine the MTD (maximum tolerated dose) and RP2D (Recommended phase two dose) of the combination therapy. AEB071 and COMPOUND B are administered to all patients on the Phase Ib study, and the combination dose will be evaluated for safety by increasing the dose of AEB071 in combination with a 30 mg dose of COMPOUND B.

The objective of the Phase II part of this study is to assess disease response by using objective measurements of tumor size, and to further characterize safety and tolerability. To aid in this evaluation, patients are centrally randomized in a 1:1 fashion to receive either MTD/RP2D for the AEB071 and COMPOUND B combination BID or 45 mg COMPOUND B BID (twice daily) only.

Both AEB071 and COMPOUND B are administered orally BID (twice daily) at the doses specified in Table below on a daily basis during each 28-day cycle.

TABLE

Dose and treatment schedule

| Study treatments | Pharmaceutical form and route of administration | Dose (total daily dose) mg | | Frequency and/or Regimen |
|---|---|---|---|---|
| | | Phase I | Phase II | |
| AEB071 | Tablet for oral use | 400 (800) | RP2D (2xRP2D) | Daily (28 day cycles) |
| COMPOUND B | Tablet for oral use | 30 (60) | 45 (90) | Daily (28 day cycles) |

Drugs are administered while tumor evaluations are under review by site staff. If it is found that the patient has progressed, treatment is stopped immediately.

The invention claimed is:

1. A pharmaceutical combination comprising or consisting of:
   a protein kinase C (PKC) inhibitor compound, or a pharmaceutically acceptable salt thereof, wherein the PKC inhibitor compound is selected from the group consisting of:
   3-(1H-indol-3-yl)-4-[2-(4-methyl-piperazin-1-yl)-quinazolin-4-yl]-1H-pyrrole-2,5-dione,
   3-(1H-indol-3-yl)-4-[2-(piperazin-1-yl)-quinazolin-4-yl]-1H-pyrrole-2,5-dione,
   3-[2-chloro-7-[(dimethylamino)methyl]-1-naphthalenyl]-4-[7-[2-(2-methoxyethoxy)ethoxy]-1H-indol-3-yl]-1H-pyrrole-2,5-dione,
   3-[3-(4,7-diaza-spiro[2,5]oct-7-yl)-isoquinolin-1-yl]-4-(7-methyl-1H-indol-3-yl)-pyrrole-2,5-dione,
   (9S)-9-[(dimethylamino)methyl]-6,7,10,11-tetrahydro-9H,18H-5,21:12,17-dimethenodibenzo-[e,k]pyrrolo[3,4-h][1,4,13]oxadiazacyclohexadecine-18,20(19H)-dione,
   ruboxistaurin, and
   12-(2-cyanoethyl)-6,7,12,13-tetrahydro-13-methyl-5-oxo-5H-indolo(2,3-a)pyrrolo(3,4-c)-carbazole,
   or a pharmaceutically acceptable salt thereof; and
   a mitogen activated protein kinase (MEK) inhibitor compound, or a pharmaceutically acceptable salt thereof.

2. A pharmaceutical combination according to claim 1, wherein the MEK inhibitor compound is selected from the group consisting of
   6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl- 6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, and RG7420,
or a pharmaceutically acceptable salt thereof.

3. A pharmaceutical combination according to claim 1, wherein the PKC inhibitor compound is 3-(1H-indol-3-yl)-4-[2-(4-methyl-piperazin-1-yl)-quinazolin-4-yl]-1H-pyrrole-2,5-dione, or a pharmaceutically acceptable salt thereof.

4. A pharmaceutical combination according to claim 1, wherein the MEK inhibitor compound is 6-(4-bromo-2-fluorophenylamino)-7-fluoro-3-methyl-3H-benzoimidazole-5-carboxylic acid (2-hydroxyethoxy)-amide, or (S)-5-fluoro-2-(2-fluoro-4-(methylthio)phenylamino)-N-(2-hydroxypropoxy)-1-methyl-6-oxo-1,6-dihydropyridine-3-carboxamide, or a pharmaceutically acceptable salt thereof.

5. A pharmaceutical combination according to claim 1, wherein the PKC inhibitor compound is 3-(1H-indol-3-yl)-4-[2-(4-methyl-piperazin-1-yl)-quinazolin-4-yl]-1H-pyrrole-2,5-dione, or a pharmaceutically acceptable salt thereof, and the MEK inhibitor compound is 6-(4-bromo-2-fluorophenylamino)-7-fluoro-3-methyl-3H-benzoimidazole-5-carboxylic acid (2-hydroxyethoxy)-amide, or a pharmaceutically acceptable salt thereof.

6. A pharmaceutical combination according to claim 1 further comprising at least one pharmaceutically acceptable carrier.

7. A pharmaceutical combination according to claim 1 for simultaneous, separate or sequential administration.

8. A pharmaceutical combination according to claim 1, wherein (a) the PKC inhibitor compound and (b) a MEK inhibitor compound are provided in synergistically effective amounts for the treatment of a melanoma.

9. A method for treating a melanoma, comprising the simultaneous, separate or sequential administration of a therapeutically effective amount of the PKC inhibitor compound 3-(1H-indol-3-yl)-4-[2-(4-methyl-piperazin-1-yl)-quinazolin-4-yl]-1H-pyrrole-2,5-dione or a pharmaceutically acceptable salt thereof, in combination with at least one MEK inhibitor compound selected from the group comprising 6-(4-bromo-2-fluorophenylamino)-7-fluoro-3-methyl-3H-benzoimidazole-5-carboxylic acid (2-hydroxyethoxy)-amide, (S)-5-fluoro-2-(2-fluoro-4-(methylthio)phenylamino)-N-(2-hydroxypropoxy)-1-methyl-6-oxo-1,6-dihydropyridine-3-carboxamide, PD0325901, PD-184352, RDEA119, GSK1120212, XL518, AS-701255, AS-701173, AS703026, RDEA436, E6201, RO4987655, JTP-74057, RG7167, or RG7420 or a pharmaceutically acceptable salt thereof, to a patient in need thereof having a melanoma.

10. A combined preparation comprising (a) one or more unit dosage forms of a PKC inhibitor compound 3-(1H-indol-3-yl)-4-[2-(4-methyl-piperazin-1-yl)-quinazolin-4-yl]-1H-pyrrole-2,5-dione or a pharmaceutically acceptable salt thereof, and (b) one or more unit dosage forms of a MEK inhibitor compound or a pharmaceutically acceptable salt thereof.

11. A pharmaceutical composition comprising a combination as defined in claim 1 and at least one pharmaceutically acceptable carrier.

12. A pharmaceutical composition according to claim 11, wherein the PKC inhibitor and MEK inhibitor are provided in synergistically effective amounts for the treatment of a proliferative disease.

13. A commercial package comprising as therapeutic agents a pharmaceutical combination as defined in claim 1 together with instructions for simultaneous, separate or sequential administration thereof for treating or delaying the progression of a melanoma.

14. A method according to claim 9, wherein the melanoma is selected from the group consisting of uveal melanoma, metastatic uveal melanoma, GNAQ mutant uveal melanoma, and GNA11 mutant uveal melanoma.

15. A method according to claim 9, wherein the MEK inhibitor is 6-(4-bromo-2-fluorophenylamino)-7-fluoro-3-methyl-3H-benzoimidazole-5-carboxylic acid (2-hydroxyethoxy)-amide.

16. A method according to claim 15, wherein the melanoma is selected from the group consisting of uveal melanoma, metastatic uveal melanoma, GNAQ mutant uveal melanoma, and GNA11 mutant uveal melanoma.

17. A pharmaceutical combination according to claim 5 for simultaneous, separate or sequential administration.

18. A pharmaceutical combination according to claim 17, wherein the melanoma is selected from the group consisting of uveal melanoma, metastatic uveal melanoma, GNAQ mutant uveal melanoma, and GNA11 mutant uveal melanoma.

19. A pharmaceutical combination according to claim 5, wherein the PKC inhibitor compound and the MEK inhibitor compound are provided in synergistically effective amounts for the treatment of a melanoma.

* * * * *